United States Patent [19]

Elbein

[11] Patent Number: 5,753,483
[45] Date of Patent: May 19, 1998

[54] PURIFIED HOMOGENEOUS UDP-GLCNAC (GALNAC) PYROPHOSPHORYLASE

[75] Inventor: Alan D. Elbein, Little Rock, Ark.

[73] Assignee: University of Arkansas, Little Rock, Ark.

[21] Appl. No.: 437,140

[22] Filed: May 5, 1995

[51] Int. Cl.⁶ .................. C12N 9/16; C12N 9/14
[52] U.S. Cl. ........................... 435/196; 435/194
[58] Field of Search .................. 435/196, 233, 435/194

[56] References Cited

U.S. PATENT DOCUMENTS

| 4,604,349 | 8/1986 | Seno et al. | 435/15 |
| 5,276,170 | 1/1994 | Kirk et al. | 552/8 |

*Primary Examiner*—Blaine Lankford
*Attorney, Agent, or Firm*—Benjamin Aaron Adler

[57] ABSTRACT

The present invention provides the enzyme UDP-N-acetylglucosamine pyrophosphorylase in isolated and purified form. Also provided is a various method of using and preparing this purified, homogeneous enzyme.

3 Claims, 9 Drawing Sheets

PURIFIED HOMOGENEOUS UDP-GLCNAC (GALNAC) PYROPHOSPHORYLASE

FEDERAL FUNDING NOTICE

The present invention was supported by grants from the National Institutes of Health (DK-21800 and HL-17783). Consequently, the United States government has certain rights in this invention.

BACKGROUND OF THE INVENTION

1. Field of the Invention

The present invention relates generally to the fields of enzymology and carbohydrate chemistry. More specifically, the present invention relates to purified, homogeneous UDP-GlcNAc pyrophosphorylase and uses thereof.

2. Description of the Related Art

N-acetylglucosamine (GlcNAc) is a very important sugar in complex carbohydrates since it is a component of N-linked oligosaccharides (1), O-linked oligosaccharides (2) and glycolipids (3), and recently has been demonstrated to be linked in O-glycosidic linkage to serine and threonine residues on nuclear proteins (4), and perhaps other proteins. Thus, a key enzyme in the production of GlcNAc polymers is UDP-GlcNAc pyrophosphorylase, the enzyme that catalyzes the formation of UDP-GlcNAc via the following reaction:

The UDP-GlcNAc pyrophosphorylase was first partially purified from calf liver and from *Staphylococcus aureus* by Strominger and Smith, and various properties of the enzyme were determined. Those enzyme preparations utilized UDP-GalNAc as a substrate at about 2.8% of the rate of the phosphorolysis with UDP-GlcNAc, but it was not clear whether that activity was due to a contaminating pyrophosphorylase. With the partially purified enzyme, the rate of UDP-glucose pyrophosphorolysis was about 30% of the rate with UDP-GlcNAc. The pyrophosphorylase was also partially purified from calf brain and that enzyme also utilized UDP-glucose at about 36% of the rate with UDP-GlcNAc.

The prior art is deficient in the lack of a purification of the UDP-GlcNAc pyrophosphorylase to homogeneity for specific uses. The present invention fulfills this longstanding need and desire in the art.

SUMMARY OF THE INVENTION

In the present invention, the pyrophosphorylase that condenses UTP and GlcNAc-1-P was purified 9,500 fold to homogeneity from the soluble fraction of pig liver extracts. At the final stage of purification, the enzyme was stable and could be kept for at least 4 months in a freezer with only slight loss of activity. On native gels, the purified enzyme showed a single protein band, and this band was estimated to have a molecular weight of about 125 kDa on Sephracryl S-300. SDS-PAGE indicated that the enzyme was a heterodimer with subunits of 64 and 55 kDa. The purified enzyme showed a very unusual specificity in that it preferred UDP-GalNAc over UDP-GlcNAc as a substrate (in the reverse direction), and GalNAc-1-P over GlcNAc-1-P in the forward direction. This activity for synthesizing UDP-GalNAc was not due to epimerase activity, since no UDP-GalNAc could be detected when the enzyme was incubated with UDP-GlcNAc for various periods of time. Furthermore, when the enzyme was incubated with UTP and GlcNAc-1-P, the only nucleoside diphosphate hexosamine formed was UDP-GlcNAc. The pyrophosphorylase required a divalent cation, with Mn++ being best at 0.5 to 1 mM, and the pH optimum was between 8.5 and 8.9. The enzyme was reacted with an azido-containing UDP-GlcNAc photoaffinity probe $[^{125}I]$-$N_3$-salicyclic acid-allylamine-UDP-GlcNAc, exposed to UV light, and run on SDS gels. Both subunits became labeled by this probe and labeling was saturable with increasing concentrations of probe. In addition, labeling was efficiently blocked by adding unlabeled UDP-GlcNAc but also to a lesser extent by UDP-GalNAc and UDP-glucose.

In one embodiment of the present invention, there is provided the enzyme UDP-N-acetylglucosamine pyrophosphorylase in isolated and purified form.

In another embodiment of the present invention, there is provided polyclonal antiserum recognizing the enzyme UDP-N-acetylglucosamine pyrophosphorylase.

In yet another embodiment of the present invention, there is provided a photoaffinity label for labeling UDP-GlcNAc-recognizing enzymes. In one embodiment, the photoaffinity label of the present invention is $[^{125}I]$-Na-salicylate-alkyamine-UDP-GlcNAc. In another embodiment, the photoaffinity label of the present invention is $N_3$-UDP$[^{32}P]$-GlcNAc.

In yet another embodiment of the present invention, there is provided a method of labeling UDP-GlcNAc-recognizing enzymes, comprising the steps of:

a) attaching a radioactively labeled azido-UDP-GlcNAc to an enzyme of interest to form a mixture;

b) activating said mixture by exposing the mixture to ultraviolet radiation;

c) separating out the enzyme from said mixture; and d) measuring the amount of radioactively labeled enzyme.

In yet another embodiment of the present invention, there is provided a method of preparing the precursor UDP-GalNAc and a method of labeling GalNaAc transferases.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows the separation on Pentyl-Sepharose. FIG. 1B shows the separation on Heparin-Sepharose. FIG. 1C shows the separation on IDA-Sepharose. Details of procedures are presented in the methods section along with the enzymatic assays used to measure activity. Profiles A–C indicate enzymatic activity by O---O, and amount of protein by O---O.

FIG. 2A shows SDS gels of the enzyme fraction: lane 1, crude extract lane 2: ammonium sulfate fraction; lane 3: 6-200 elution: lane 4: Pentyl-Sepharose elution; lane 5, fraction from Heparin-Sepharose; lane 6: fraction from Blue-Sepharose; lane 7: known protein markers. FIG. 2B shows native gels as follows: lane 1: crude extract; lane 2: ammonium sulfate fraction; lane 3: 6-200 fraction: lane 4: Heparin-Sepharose elution; lane 5: Zinc-Sepharose fraction; lane 6: Blue-Sepharose elution.

DETAILED DESCRIPTION OF THE INVENTION

Figure 1A:
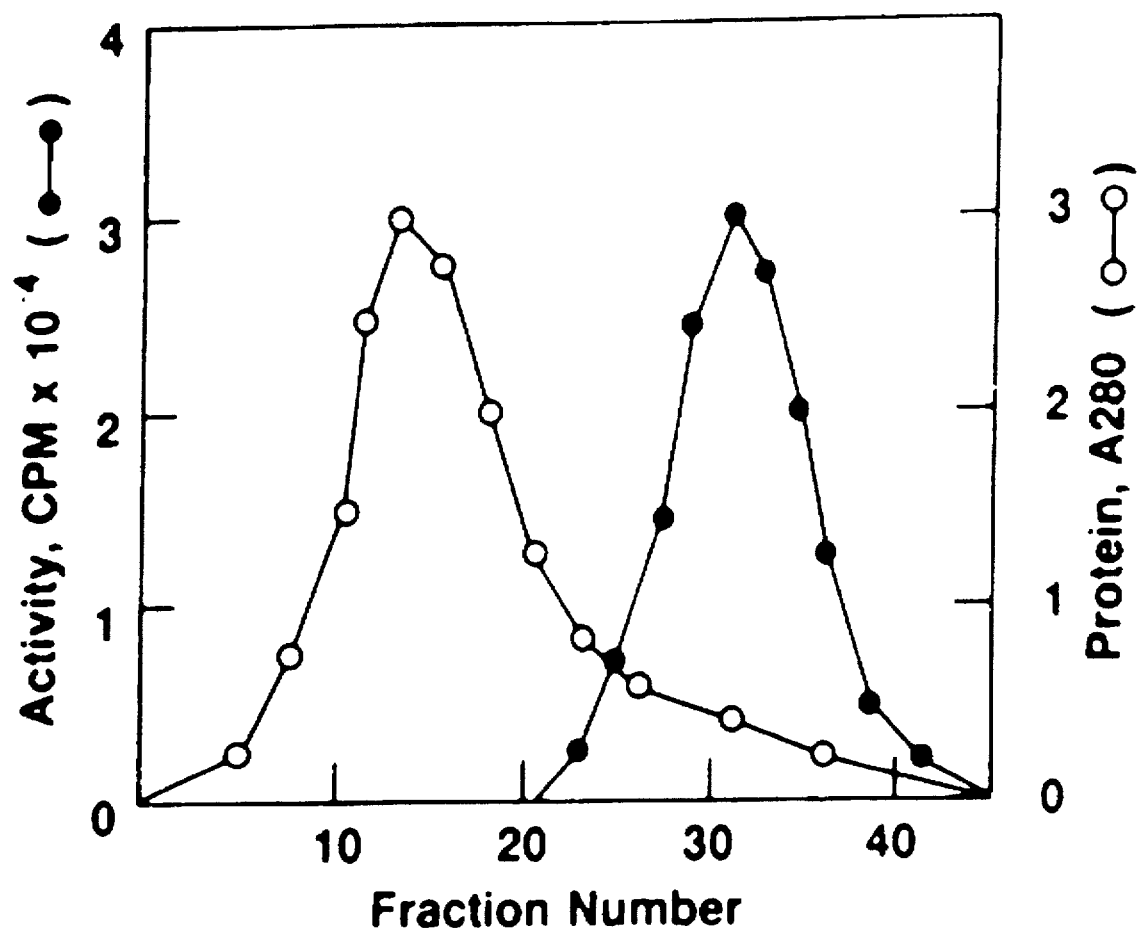
FIGS. 1A–1C show the column chromatographic steps in the purification of UDP-GlcNAc pyrophosphorylase. The profiles shown are as follows.

The present invention is directed to the enzyme UDP-N-acetylglucosamine pyrophosphorylase in isolated and purified form. Preferably the enzyme is isolated and purified to homogeneity from pig liver. The enzyme UDP-N-acetylglucosamine pyrophosphorylase has the following biochemical characteristics: the enzyme has a molecular weight of about 125 kilodaltons when analyzed by sodium dodecyl sulfate polyacrylamide gel electrophoreses, has an optimal pH of from about pH 8.5 to about 8.9, the purified enzyme being stable for at least four months when stored at −35° C. and wherein said enzyme catalyzes the formation of UDP-N-acetylglucosamine. Generally, the enzyme requires manganese for optimal activity. The enzyme UDP-N-acetylglucosamine pyrophosphorylase is also shown to catalyze the pyrophosphorylsis of UDP-N-acetylgalactosamine and UDP-glucose.

The present invention is directed to polyclonal antiserum recognizing the enzyme UDP-N-acetylglucosamine pyrophosphorylase.

The present invention is directed to a photoaffinity label for labeling UDP-GlcNAc-recognizing enzymes. In one embodiment, the photoaffinity label of the present invention is [$^{125}$I]-Na-salicylate-alkyamine-UDP-GlcNAc. In another embodiment, the photoaffinity label of the present invention is $N_3$-UDP[$^{32}$P]-GlcNAc.

The present invention is directed to a method of labeling UDP-GlcNAc-recognizing enzymes, comprising the steps of: a) attaching a radioactively labeled azido-UDP-GlcNAc to an enzyme of interest to form a mixture; b) activating said mixture by exposing the mixture to ultraviolet radiation; c) separating out the enzyme from said mixture; and d) measuring the amount of radioactively labeled enzyme. Generally, the enzyme may be separated out using techniques known in the art. Preferably, the enzyme of interest is separated out by precipitating the enzyme using trichloacetic acid (TCA and running the precipitate on a sodium dodecyl sulfate gel.

The following examples are given for the purpose of illustrating various embodiments of the invention and are not meant to limit the present invention in any fashion.

EXAMPLE 1

Materials

UDP-[$^3$H]GlcNAc (6 Ci/mmol) and [5,6-$^3$H]UTP (30 Ci/mmol) were purchased from ICN. All other nucleoside mono-, di-, and triphosphates, as well as sugar-phosphates, were obtained from Sigma Chemical Co. The following enzymes were also from Sigma Chemical Co.: glucose-6-P dehydrogenase (EC 1.1.1.49), nucleoside diphosphate kinase (EC 2.7.4.6), hexokinase (EC 2.7.1.1), inorganic pyrophosphatase (EC 3.6.1.1) and alkaline phosphatase (EC 3.1.31). Various adsorbents were obtained from the following sources: DEAE cellulose (DE-52) from Whatman Chemical Separations, Ltd.; Sephadex G-200, Polybuffer Exchanger 94 and Heparin-Sepharose from Pharmacia LKB Biotechnology, Inc.; Sephacryl S-300, Blue- Sepharose, Pentyl-Sepharose, UTP-Sepharose, UDP-hexanolamine-Sepharose, IDA-Sepharose and Protein A-Sepharose were from Sigma Chemical Co. PEI cellulose TLC plates were purchased from EM Science, cellulose TLC plates were from Kodak and silica gel TLC plates were from Merck. The following materials were obtained from Biorad: sodium dodecylsulfate (SDS), acrylamide, bisacrylamide, Coomassie blue, protein assay reagent, hydroxyapatite, nitrocellulose, horseradish peroxidase conjugated goat-antirabbit IgG (H+L) antibodies, and Immobilon P membranes. All other chemicals were obtained from reliable commercial sources and were of the best grade available.

EXAMPLE 2

Pyrophosphorylase Assay

The UDP-HexNAc pyrophosphorylase could be assayed either in the forward direction (i.e., synthesis of nucleoside diphosphate GlcNAc (GalNAc)), or in the reverse direction (i.e., formation of UTP). When measured in the reverse direction, either a direct assay or an indirect assay could be used. For the direct assay, pyrophosphorylase activity was measured by determining the production of [$^3$H]GlcNAc-1-P from UDP-[$^3$H]GlcNAc and inorganic pyrophosphate, essentially as previously described by Strominger, J. L. and Smith, M. S., *J. Biol. Chem.* 234: 1822–1827 (1959). The incubation mixtures contained the following components in a final volume of 50 µl: 5 mM sodium pyrophosphate, 250 uM UDP-[$^3$H]GlcNAc (2.2 Ci/mmol), 100 mM Tris HCl buffer, pH 8.5, 2 mM MgCl$_2$, and various amounts of enzyme at the different stages of purification. After an incubation of 5 minutes at 37° C., the reactions were terminated by the addition of 0.5 ml of 5% trichloroacetic acid, and the nucloeotides were absorbed on charcoal by the addition of 0.3 ml of acid washed charcoal (150 mg/ml of Darco G-50 in water). The suspension was vortexed vigorously for 2 minutes, and was then centrifuged in a microfuge. The supernatant liquid was removed and saved, and the charcoal was washed with 1 ml of water. The supernatant liquid from this wash was combined with the first supernatant liquid, and an aliquot was removed and counted, as a measure of the formation of GlcNAc-1-P.

For the indirect assay, a modification of the spectrophotometric method of Munch-Petersen, (1956) *Acta Chim. Scand.* 10, 928–934 was used to measure the amount of UTP formed when unlabeled UDP-GlcNAc (or GalNAc) was incubated with purified enzyme fractions in the presence of inorganic pyrophosphate. The assay mixtures contained 50 mM Tris-HCl buffer, pH 7.5, 1 mM MgCl$_2$, 0.5 mM ADP, 1 mM glucose, 0.5 mM NADP, 1 mM inorganic pyrophosphate, 2 mM UDP-HexNAc and 2.5 units each of nucleoside diphosphate kinase, hexokinase and glucose-6-P dehydrogenase. The reactions were started by the addition of the pyrophosphorylase and the rate of NADPH formation was measured at 340 nm.

The UDP-GlcNAc(GalNAc) could also be assayed in the forward direction by measuring the formation of UDP-[$^3$H] GlcNAc, as indicated below. Incubation mixtures contained the following components in a final volume of 40 ul: 50 mM Tris-HCl buffer, pH 7.5, 1 mM MgCl$_2$, 1 µM [$^3$H]UTP (1.7 Ci/mmol), 10, µM sugar-1-P, 1 unit of inorganic pyrophosphatase and various amounts of the UDP-GlcNAc pyrophosphorylase. After an incubation of 10 minutes at 37° C., the reaction was terminated by heating the tubes in a boiling water bath for 30 seconds. The amount of product could either be determined by measuring the amount of radioactivity that bound to DE-52 (HCO$_3$–) after treatment of the reaction mixtures with alkaline phosphatase, or the product could be detected by TLC.

EXAMPLE 3

Purification of the UDP-GlcNAc Pyrophosphorylase

Preparation of the Crude Extract

Fresh pig livers from a local slaughter house were generally used in these studies but livers, obtained fresh and quick frozen, gave equally good results. All operations were done at 4° C. unless otherwise specified. Two kg of liver were cut into small pieces (125 g), and each piece was minced for about 2 minutes in a Waring blender in 250 ml of Buffer A (20 mM Tris-HCl, pH 7.5, containing 1 mM β-mercaptoethanol and 1 mM EDTA). The homogenates were centrifuged at 12,000 rpm for 60 minutes, and the supernatant liquid was collected and the pH adjusted to 5.0 by the addition of cold 2% acetic acid. The mixture was kept on ice for 10 minutes and then was centrifuged to remove insoluble material. The supernatant liquid was saved and adjusted back to pH 7.5 by the addition of solid NaHCO$_3$.

EXAMPLE 4

Ammonium Sulfate Precipitation

Solid ammonium sulfate was added to the crude extract to a saturation of 35%, and the mixture was allowed to stand for 30 minutes on ice before removing the insoluble residue by centrifugation. The supernatant liquid was then brought to 50% saturation by the addition of appropriate amounts of solid ammonium sulfate, and the precipitate containing the active UDP-GlcNAc pyrophosphorylase, was collected and dissolved in about 500 ml of Buffer A. This ammonium sulfate fraction was then dialyzed for 24 hours against 4 L of Buffer B (20 mM Tris buffer, pH 7.5 containing 50 mM NaCl, 1 mM EDTA and 1 mM β-mercaptoethanol), and the dialysis fluid was changed 3 times during this period.

EXAMPLE 5

DEAE-cellulose Chromatography

Two 3.5×35 cm columns of DEAE cellulose were prepared and each column was washed with 1M Tris-HCl buffer, pH 7.5, until the pH was 7.5. The columns were then equilibrated with Buffer B, and half of the dialyzed ammonium sulfate fraction was added to each column. The columns were washed with Buffer B until the effluent was clear and colorless, and the pyrophosphorylase was eluted with 1 L of a 50 to 250 mM gradient of NaCl. Fractions were assayed for enzyme activity, and active fractions were pooled and concentrated to about 35 ml on an Amicon apparatus with a PM membrane.

EXAMPLE 6

Gel Filtration Chromatography

The concentrated fraction from the DEAE cellulose column was applied to a 6×95 cm column of Sephadex G-200 which had been equilibrated with Buffer A. Nine ml fractions were collected at a flow rate of 30 ml/hour, and every other fraction was assayed for activity. Active fractions were pooled and concentrated to about 12 ml on the Amicon filtration apparatus.

EXAMPLE 7

Pentyl-Sepharose Chromatography

The active peak from Sephadex was brought to 10% saturation by the addition of solid ammonium sulfate, and was applied to a 2.5×20 cm column of Pentyl-Sepharose, which had been equilibrated with 10% ammonium sulfate in Buffer A. The column was washed with the same solution and 5 ml fractions were collected at a flow rate of 20 ml/hour. Active fractions were pooled, concentrated to about 5 ml and dialyzed against 1 L of Buffer A, with 3 changes of the dialysis fluid.

EXAMPLE 8

Heparin-Sepharose Chromatography

The enzyme fraction from the previous step was applied to a 2.5×25 cm column of Heparin-Sepharose that had been equilibrated with Buffer A. The enzyme was eluted from the column with 500 ml of a 0 to 0.5M gradient of NaCl. The active fractions were pooled, concentrated to about 5 ml, and dialyzed for 6 hours against Buffer C (50 mM MES buffer, pH 7.4, containing 1M NaCl).

EXAMPLE 9

Immobilized Metal Ion Affinity Chromatography (IMAC)

A 1.4×20 cm Zn$^{++}$-charged column, containing iminodiacetic acid covalently bound to Sepharose (IDA-Sepharose), was prepared and washed with Buffer C. The enzyme fraction from EXAMPLE 8 was applied to this column, and the pyrophosphorylase activity was eluted with a 300 ml gradient of Buffer D (100 mM acetate buffer, pH 5.0, containing 1M NaCl). Fractions of 5 ml were collected and each fraction was analyzed for protein, enzymatic activity and pH. Active fractions were pooled, concentrated and dialyzed overnight against Buffer A, containing 30 mM NaCl.

EXAMPLE 10

Blue Sepharose Chromatography

The enzyme fraction from EXAMPLE 9 was added to 0.5 ml of Blue-Sepharose, contained in a Pasteur pipette. The column was washed with Buffer A, and the enzyme emerged in the wash. This fraction was concentrated and dialyzed against Buffer A. A summary of the purification procedure is presented in Table I.

TABLE I

Purification Table

| Step | Vol. | Prot. | S.A. | T.A. | Purif. | Yiel |
|---|---|---|---|---|---|---|
| Purified extract | 3960 | 213840 | 0.0016 | 334 | 1 | 100 |
| Ammonium sulfate | 675 | 62775 | 0.0053 | 329 | 3.4 | 38 |
| DEAE collection | 535 | 5083 | 0.057 | 278 | 10.4 | 83 |
| Seplealeo 9-200 | 284 | 1620 | 0.11 | 158 | 71 | 67 |
| Pentyl-Seph | 70 | 40 | 1.37 | 55 | 878 | 17 |
| Heparin-Seph | 63 | 8.2 | 2.865 | 23 | 1836 | 7 |
| Lu-Sephawn | 25 | 1.88 | 6.675 | 13 | 4278 | 6 |
| Blue Seph. | 16 | 0.34 | 14.861 | 5 | 9526 | 2 |

Abbreviations: Vol: volume (ml); prot.: protein (mg); S.A: specific activity; T.A.: total activity; purif.: purification (total); yield is in %.

EXAMPLE 11

Characterization of the Reaction Products

The reaction products, formed in either the forward direction (i.e., uridine diphosphate sugars), or in the reverse direction (i.e., UTP and sugar-i-P's), were isolated by chromatography on a 1×20 column of DEAE-cellulose ($HCO_3^-$), equilibrated in 10 mM $NH_4HCO_3$. After application of the sample, the column was washed with the same solution and the retained products were eluted with 200 ml of a linear 10 to 300 mM gradient of $NH_4HCO_3$. Fractions were analyzed for nucleotides by measuring the absorption at 260 nm, for radioactivity by scintillation counting, and for hexosamine by the Reissig test (*J. Biol. Chem.*, 217, 959–966, 1955) or the or the Elson Morgan assay (Wheat, R. W. (1966) Meth. Enzymol. 8, 60–78). Peak fractions were pooled and concentrated on a rotary evaporator and $NH_4H\,CO_3$ was removed by evaporation in the presence of triethylamine. The triethylamine was in turn removed by evaporation in the presence of methanol.

The reaction products were identified by chromatography, either directly, or following various treatments such as digestion with phosphodiesterase or alkaline phosphatase, or acid hydrolysis. Nucleotides were identified by TLC in the following systems: PEI plates developed in 0.2M and 0.4M solutions of LiCl; cellulose plates in ethanol: 1M ammonium acetate, pH 7.3 (7:3), or silica gel plates in ethanol: 1M ammonium acetate, pH 5.0 (7:3). N-acetyl-hexosamines were released from nucleotides by mild acid hydrolysis (0.01 N HCl, 100° C., 15 minutes) and identified by chromatography on borate-treated paper in n-butanol:pyridine:water (6:4:3) as described earlier by Cardini and Leloir, (1953) *Arch. Biochem. Biophys.*, 45, 317–324.

Sugars were detected by the method of Reissig cited above. Deacetylation of the N-acetyl-hexosamines in 2N HCl at 100° C. for 2 hours gave aminosugars that were analyzed by paper chromatography in butanol:pyridine:$H_2O$ (6:4:3), and detected by the silver nitrate dip or the Elson-Morgan spray.

EXAMPLE 12

Polyacrylamide Gel Electrophoresis

Native PAGE was performed as described by Laemli with an 8% gel and a discontinuous buffer system, but under non-denaturing conditions. Two samples were run in parallel: One lane was stained with Coomassie Blue to detect protein bands and the other was cut into 1 cm pieces and each piece was crushed in 200 µl of Buffer A and incubated overnight in the cold to elute the enzyme. The gel was removed by centrifugation and the supernatant liquid was analyzed for pyrophosphorylase activity.

SDS-PAGE was done as described by Kaushal, et al., *Biochemistry* 29, 2168–2176 (1990). Prior to electrophoresis, protein samples were mixed with sample buffer (62 mM Tris-HCl, pH 6.8, 5% β-mercaptoethanol, 2% SDS, 10% glycerol and 0.002% bromophenol blue) and heated in a boiling water bath for 5 minutes.

EXAMPLE 13

Determination of Native Molecular Weight and pI Value

The molecular weight of the enzyme was estimated from its elution profile on a calibrated 1.7×112 cm column of Sephacryl S-300, equilibrated with 50 mM Tris-HCl buffer, pH 7.5 containing 0.1 M NaCl. The following proteins were run as standards: carbonic anhydrase, 29 kDa; creatine kinase, 80 kDa; lactic acid dehydrogenase, 140 kDa; β-amylase, 200 kDa; apoferitin, 443 kDa; thyroglobulin, 660 kDa. The isoelectric point was determined by chromatofocusing with the use of a Polybuffer Exchanger 94 column (1×35 cm). The column was equilibrated with 25 mM histidine-HCl buffer, pH 6.5. The formation of the pH gradient and the elution of the enzyme were done using a 10-fold diluted Polybuffer 74, pH 4.5, according to the Pharmacia protocol. The pyrophosphorylase was eluted at pH 5.3.

EXAMPLE 14

Antibody Production and Western Blotting

Polyclonal antibody against the native enzyme (using a total of 220 µg of protein) was prepared in rabbits following standard procedures as described by Harlow and Lane, *Antibodies, a Laboratiory, Manual.* Cold Spring Harbor Lab. pp. 53–139 (1988).

For immunoblot analysis, proteins were electrophoretically transferred to Immobilon and treated with crude antiserum at a 1:4000 dilution. Immunoprecipitation was done by incubating enzyme with crude antisera and precipitating the complex with a mixture of Protein A-Sepharose and Protein G-Sepharose.

EXAMPLE 15

Purification Of The UDP-GlcNAc Pyrophosphorylase

Figure 1B:
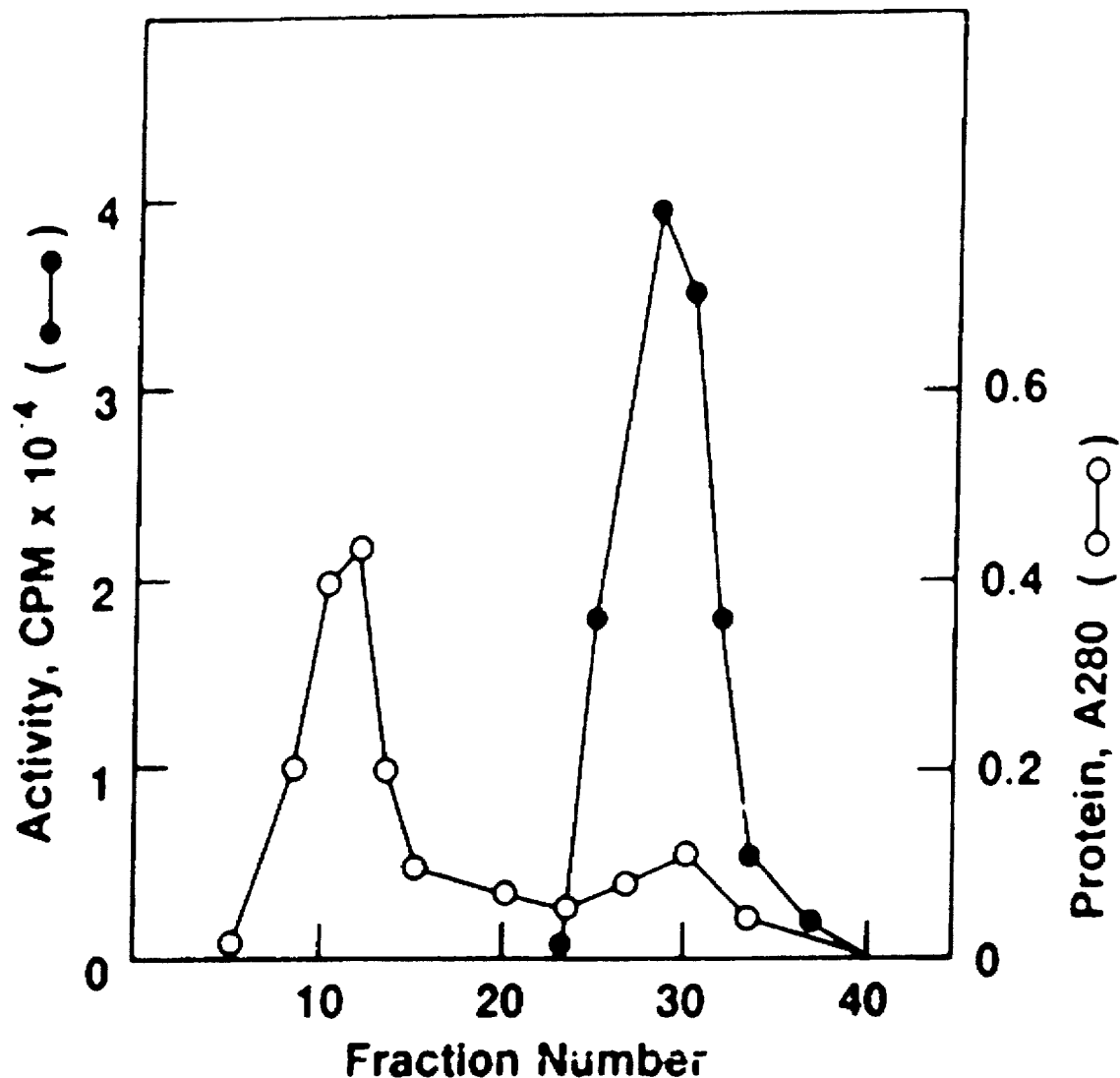
Figure 1C:
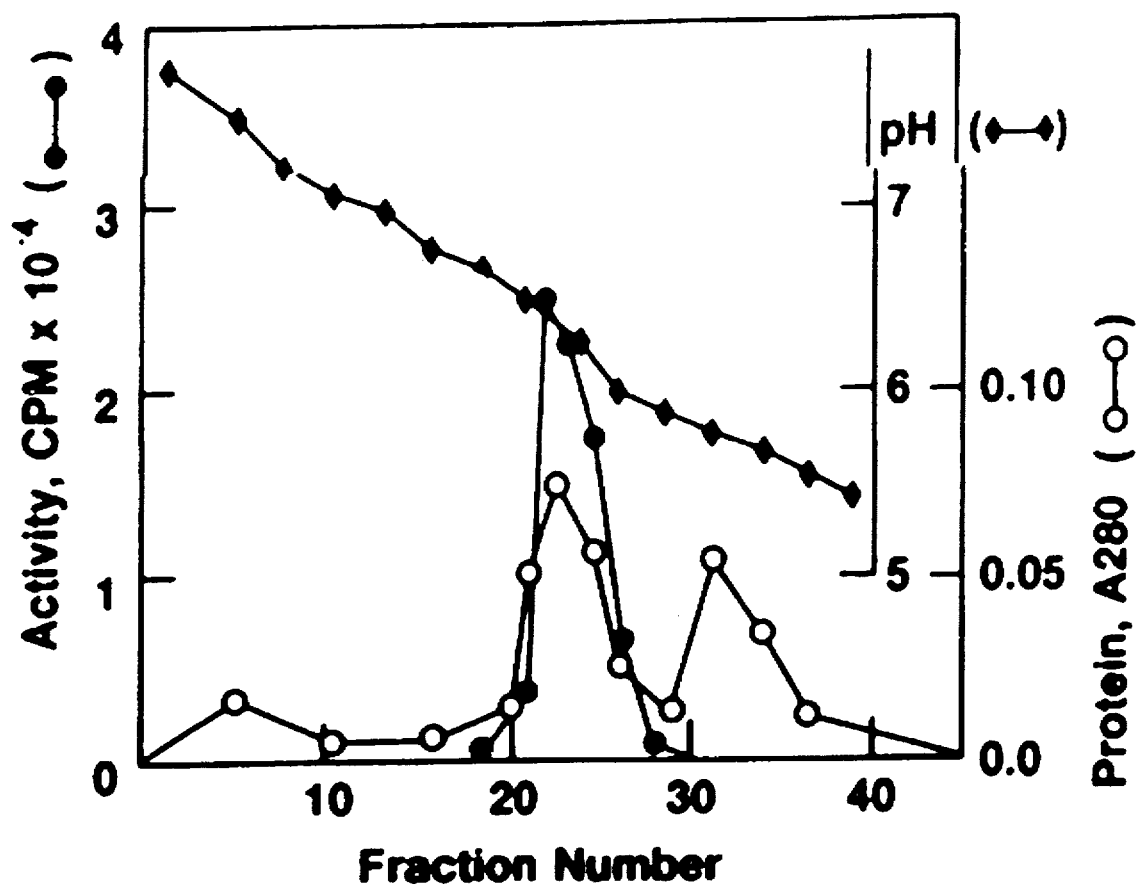

The UDP-HexNAc pyrophosphorylase was purified from pig liver following the procedure above. The liver extract was first clarified by acid treatment, followed by ammonium sulfate fractionation and DEAE cellulose chromatography. This chromatography gave a 10-fold purification, and gel filtration on a long column gave another 7-fold purification. FIG. 1 presents the profiles of subsequent purification steps on Pentyl-Sepharose (1A), Heparin-Sepharose (1B) and IDA-Sepharose (1C) columns. These three steps resulted in more than 60-fold purification. Thus, hydrophobic chromatography on the Pentyl-Sepharose column resolved the enzyme from the bulk of inactive protein and resulted in a 12-fold increase in specific activity while the next two steps also removed substantial amounts of protein and improved the specific activity. The total purification scheme, summarized in Table I, resulted in a 9500-fold purification of the UDP-HexNAc pyrophosphorylase with a final yield of about 2%. From 2 kg of pig liver, about 340 μg of pure protein were isolated, and this proved to be enough protein to obtain amino acid sequence information and to prepare antibodies in a rabbit.

EXAMPLE 16

Properties of the Purified Pyrophosphorylase

Molecular Weight and Homogeneity of the Pyrophosphorylase

Figure 2A:
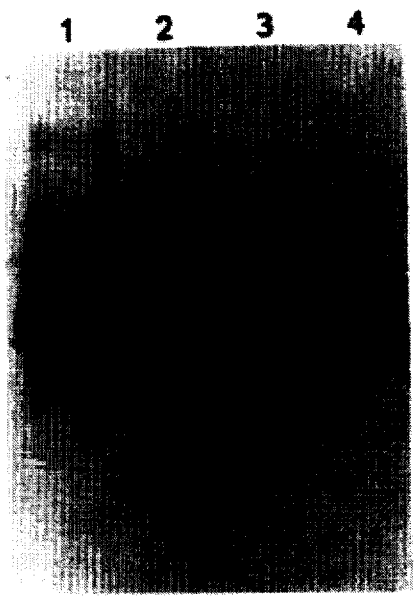
FIGS. 2A–2B show the profile of purification by gel electrophoresis of UDP-GlcNAc Pyrophosphorylase at various stages.

The enzyme from the final stage of purification showed a single band on native gels as demonstrated in FIG. 2A (lane 6). This band, eluted from the gels, showed strong UDP-GlcNAc pyrophosphorylase activity indicating that it was the desired enzyme. Based on the migration of this purified protein on a column of Sephacryl S-300, as compared to a number of standard proteins, the molecular weight of the native enzyme was estimated to be about 124 kDa (data not shown).

Figure 2B:
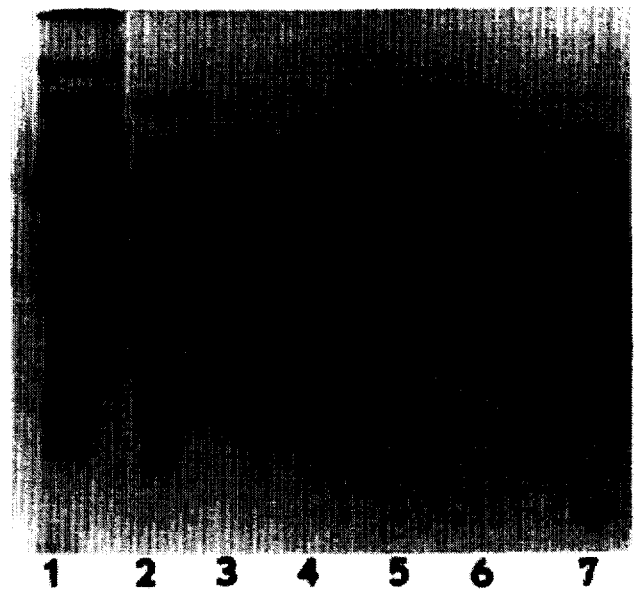

FIG. 2B shows SDS-PAGE gels of the pyrophosphorylase at various stages of purification. In the final preparation (lane 6), 2 bands were detected having molecular weights of 64 and 55 kDa. These may be subunits of the enzyme and that the native enzyme is a heterodimer composed of an αx-subunit (64 kDa) and a β-subunit (55 kDa).

Stability

The purified enzyme was quite stable when stored on ice in Buffer A, containing 0.05% sodium azide. Under these conditions, the half life of the enzyme was estimated to be about 5 months. The enzyme was also stable to storage in the frozen state, and more than 90% of the activity still remained after 4 months of storage. The best stability was observed upon storage at pH 6.5–7.5.

Kinetic Constants

The activity was dependent on substrate concentrations in the following ways: In the forward direction, the apparant $K_m$ for GlcNAc-1-P (at 1 mM UTP) was 2.0 mM and the $V_{max}$ was 3.1 nmol/min, while the $K_m$ for GalNAc-1-P was 5.5 mM and the $V_{max}$ was 7.1 nmol/minute. The $K_m$ for the other substrate, UTP, was also measured at 10 mM GlcNAc-1-P and was found to be 2.5 mM and the $V_{max}$ was 4.8 nmol/minute. Since the enzyme also utilizes glucose-1-P as a substrate, the $K_m$ for this substrate was measured (also at 1 mM UTP) and was found to be 66.6 mM while the $V_{max}$ was 1.7 nmol/minute. In the reverse direction, the $K_m$ and $V_{max}$ values for each nucleotide were as follows (at 1 mM inorganic pyrophosphate): UDP-GlcNAc, $K_m$ =0.05 mM, $V_{max}$ =22.2 nmol/min; UDP-GalNAc, $K_m$=0.20 mmol, $V_{max}$ =31.3 nmol/min.; UDP-Glc, $K_m$ =28.6 mmol, $V_{max}$ =25 nmol/min. The $K_m$ for inorganic pyrophosphate (at 1 mM UDP-GlcNAc) was estimated to be 0.07 mmol and the $V_{max}$ was 20 nmol/min. (data not shown).

pH Optimum

The pH optimum for the pyrophosphorylase was measured in the reverse direction by both the radioactive assay and a colorimetric assay as described above. In both cases, the pH optimum was between 8.5 and 8.9. This pH profile is quite different than those described for the UDP-GlcNAc pyrophosphorylase of *Staphylococcus aureus* and calf liver, which had pH optima of 7.2, or that from brain with a pH optimum of 8.0.

Metal Ion Requirements

The pyrophosphorylase showed absolute requirements for a divalent cation for activity as indicated in Table II. The effectiveness of the ion activators was in the order: $Mn^{++}$, $Co^{++}$, $Mg^{++}$, and $Ni^{++}$, but measurable activity was also observed with $Zn^{++}$, $Cu^{++}$ and $Fe^{++}$. Other ions such as $Fe^{+++}$, $Ca^{++}$ and $Hg^{++}$ were ineffective. The concentration curves of these metal ion effectors indicated that $Mn^{++}$, $Co^{++}$ and $Mg^{++}$ were the most effective in the range of 0.5 to 1.0 mM. Higher concentrations of these ions resulted in a considerable decrease in the activation. For the UDP-GlcNAc pyrophosphorylase from brain, $Mg^{++}$ was the most effective cation, followed by $Co^{++}$ and then $Mn^{++}$.

TABLE II

Effects of Metal Ions on Pyrophosphorylase Activity

| Metal Ion (1 mM) | Activity (nmole) | (%) |
|---|---|---|
| Mn++ | 4.89 | 100 |
| Co++ | 3.6 | 74 |
| Mg++ | 4.2 | 86 |
| Ni++ | 1.3 | 27 |
| Zn++ | 0.53 | 11 |
| Cu++ | 0.42 | 9 |
| Fe++ | 0.40 | 8 |
| Fe+++ | 0 | 0 |
| Ca++ | 0 | 0 |
| Hg++ | 0 | 0 |

Substrate Specificity

The substrate specificity of the purified enzyme was examined in both the forward and the reverse direction. Table III shows that in the forward direction, the enzyme actually prefers GalNAc-1-P slightly over GlcNAc-1-P, while other sugar phosphates such as Glc-1-P and Gal-1-P may act as substrates but to a much lower degree. On the other hand, in the reverse direction, the pyrophosphorylase showed greatest activity with UDP-GalNAc (100%), while UDP-glucose was somewhat less effective (83%), followed by UDP-GlcNAc (66%). These data are shown in Table IV. Of other UDP-GlcNAc pyrophosphorylases, the sheep brain enzyme was most active with UDP-GlcNAc, but also showed some activity with UDP-glucose (36%) but not with UDP-GalNAc. Somewhat similar results were observed with the calf liver enzyme. The enzyme from bacteria acted on UDP-GlcNAc and showed only marginal activity on UDP-GalNAc (2.6%).

TABLE III

Specificity of Pyrophosphorylase (Forward Direction)

| Sugar Phosphate (5 mM) UT = 5 mM | Activity (nmole/min) | Relative Activity % |
|---|---|---|
| GalNAc-1-P | 5.28 | 100 |
| GlcNAc-1-P | 4.83 | 91 |
| Glc-1-P | 0.20 | 4 |
| Gal-1-P | 0.14 | 3 |
| GlcN-1-P | 0.10 | 2 |
| GalN-1-P | 0 | — |

TABLE IV

Specificity of Pyrophosphorylase (Reverse Direction)

| Sugar Phosphate (5 mM) PP = 1 mM | Activity (nmole/min) | Relative Activity % | Km (mM) |
|---|---|---|---|
| UDP-GalNAc | 19.7 | 100 | 0.2 |
| UDP-Glc | 16.4 | 83 | 28.6 |
| UDP-GlcNAc | 13.0 | 66 | 0.045 |
| UDP-MAN | 1.8 | 9 | — |
| UDP-GlcCOOH | 1.4 | 7 | — |
| UDP-GalCOOH | 1.3 | 7 | — |
| UDP-Gal | 1.0 | 5 | — |
| ADP-Glc | 0.6 | 3 | — |

Effect of Inhibitors

Figure 3:
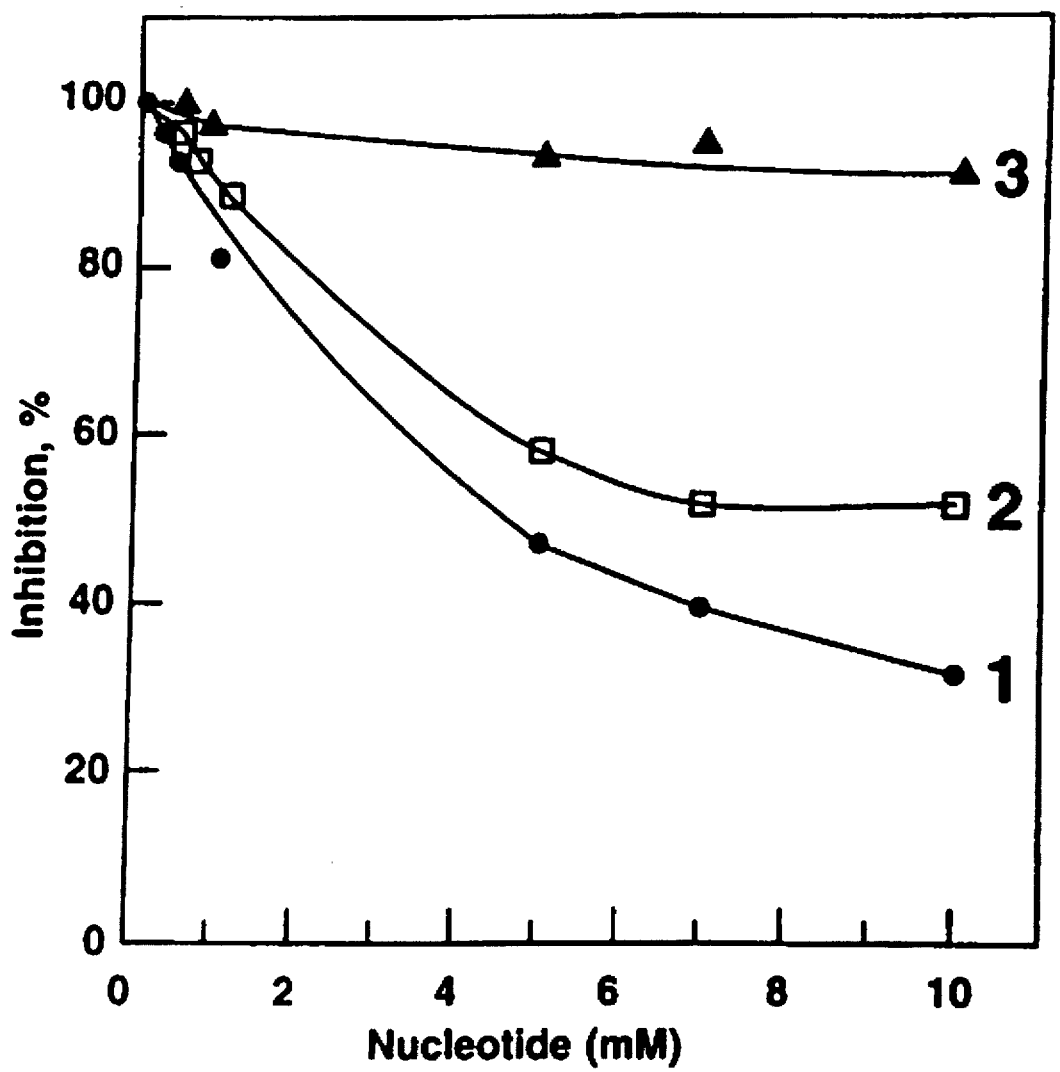
FIG. 3 shows inhibition of UDP-GlcNAc pyrophosphorylase activity by nucleotides. The pyrophosphorolysis of UDP-[$^3$H]GlcNAc was measured in the presence of various amounts of UDP-GalNAc (curve 1, O---O), UDP-glucose (curve 2, ---), or UDP-xylose or UDP-glucuronic acid (curve 3, ---). Activity was measured in the reverse direction (i.e., production of GlcNAc-1-P) as indicated.

Since the enzyme catalyzes the pyrophosphorolysis of three substrates, UDP-GlcNAc, UDP-GalNAc and UDP-Glc, it was of interest to determine how the presence of one sugar nucleotide would affect the phosphorolysis of another sugar nucleotide. In addition, if one of these nucleotides did in fact inhibit the utilization of another, it would support the specificity data that a single enzyme utilizes all of these substrates. FIG. 3 shows that the reaction with UDP-[$^3$H] GlcNAc was inhibited by increasing concentrations of UDP-GalNAc and UDP-glucose, but not by UDP-xylose or UDP-glucuronic acid.

A variety of other inhibitors were tested, including various sulfhydryl reagents and metal chelators. As indicated in Table V, 1 mM N-ethylmaleimide gave 72% inhibition of the pyrophosphorylase activity, while iodoacetamide at 1 mM gave 44%, and 1 mM Hg$^{++}$ gave 84%. Various metal chelators such as EDTA, EGTA and 1, 10-phenanthroline did not inhibit (as long as sufficient Mn$^{++}$ was added), nor did inorganic phosphate, even at 10 mM concentrations.

TABLE V

Putative Inhibitors of Pyrophosphorylase

| Inhibitor | Concentration (mM) | Inhibition (%) |
|---|---|---|
| N-ethylmaleimide | 0.01 | 3 |
|  | 0.10 | 46 |
|  | 1.0 | 72 |
| Iodoacetamide | 0.10 | 10 |
|  | 0.1 | 21 |
|  | 1.0 | 44 |
| Hg++ | 0.01 | 39 |
|  | 0.1 | 67 |
|  | 1.0 | 86 |
| Ca++ | 0.1 | 0 |
|  | 1.0 | 28 |
| Zn++ | 0.1 | 3 |
|  | 1.0 | 38 |
| Dithiothreitol | 0.1 | 21 |
|  | 1.0 | 62 |
| O-Phenanthroline | 0.1 | 5 |
|  | 1.0 | 16 |
| EGTA | 0.1 | 8 |
|  | 1.0 | 13 |
| ETTA | 0.1 | 5 |
|  | 1.0 | 13 |

Tissue Occurrence

Preliminary determinations of the pyrophosphorylase activity in various pig tissues were done using UDP-[$^3$H] GlcNAc as the substrate. The following levels of enzymatic activity were obtained (nmol/mg$^{-1}$/min$^{-1}$): salivary gland, 3.65; pancreas, 1.69; lung, 1.16; brain, 0.86; liver, 0.48; spleen, 0.44; aorta, 0.43; kidney, 0.12 and heart, 0.12.

EXAMPLE 17

Identification Of The Products Of The Pyrophosphorylase Activity

Figure 4:
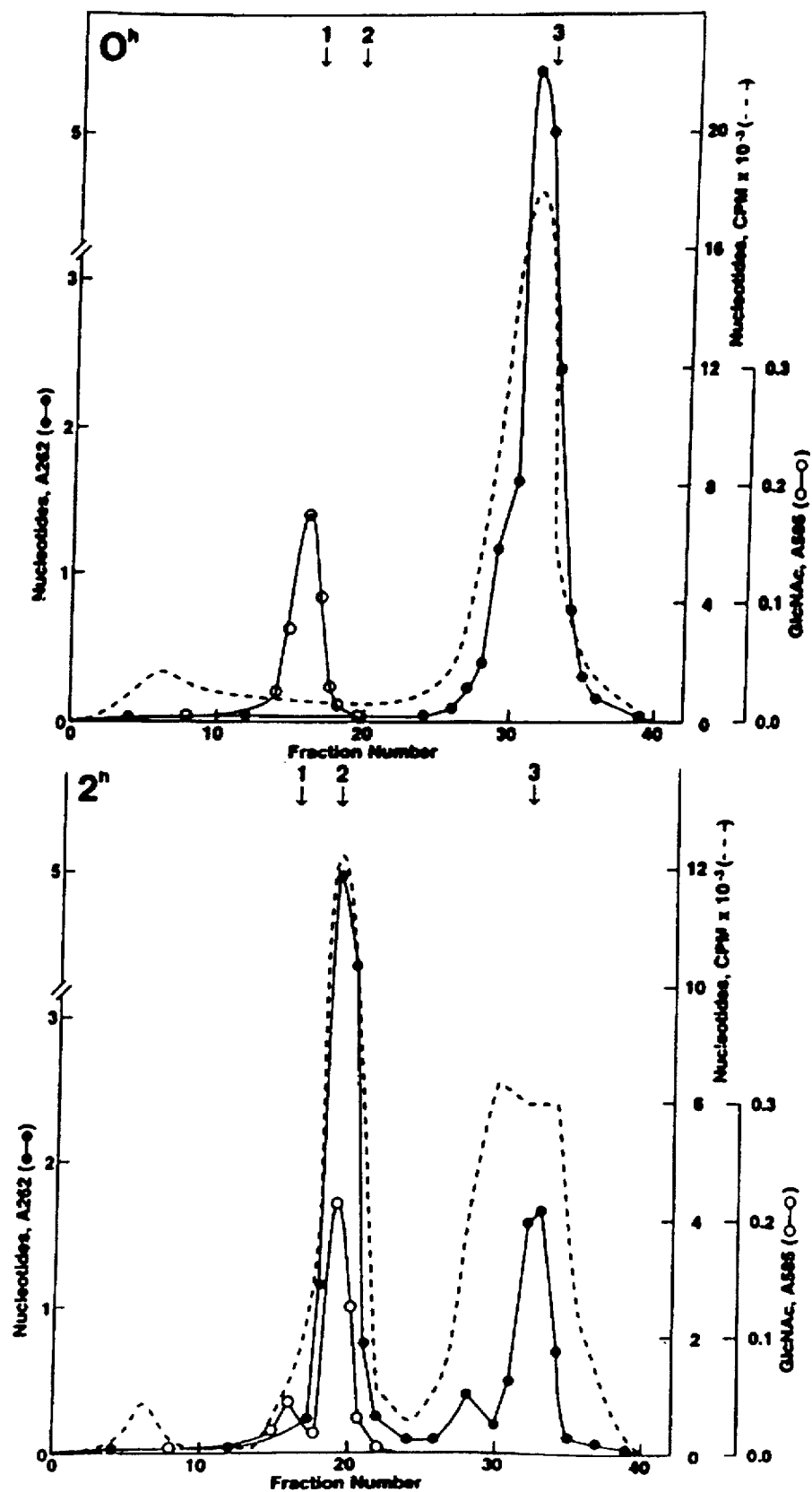
FIG. 4 shows the isolation and characterization of reaction product as UDP-GlcNAc. Enzyme was incubated with [$^3$H]UTP, Mg$^{++}$ and GlcNAc-1-P for up to 2 hours in the presence of inorganic pyrophosphatase, and the reaction mixtures were applied to columns of DE-52. Sugar-Ps and nucleoside diphosphate sugars were separated with a gradient of $NH_4(HCO_3)$. Fractions were analyzed for radioactivity (---), for GlcNAc by a calorimetric assay (O---), and for nucleotide content (O---). The upper profile is a control without incubation while the lower profile is after a 2 hour incubation.

The purified enzyme was incubated with [$^3$H]UTP, Mg$^{++}$, and GlcNAc-1-P in the presence of inorganic pyrophosphatase, and the reaction was terminated after 2 hours. After deproteinization, the aqueous phase was applied to a column of DE-52 and sugar phosphates and nucleoside diphosphate sugars were separated with a gradient of NH$_4$HCO$_3$, as shown in FIG. 4. A peak of radioactivity, representing 79% of the total (7.9 umol), emerged in the UDP-GlcNAc area of the column. This radioactive material was susceptible to the action of phosphodiesterase, but not to that of alkaline phosphatase. The peak was pooled and subjected to TLC in 3 different solvent systems as described above. In each case, the material co-chromatographed with authentic UDP-GlcNAc, and was clearly separated from GlcNAc-1-P. Mild acid hydrolysis (0.05 N HCl, 100° C., 15 minutes) gave a single radioactive spot corresponding to GlcNAc on borate-treated paper in n-butanol:pyridine:water (6:4:3). Deacetylation of the presumptive GlcNAc gave an amino sugar with the same migration as glucosamine, and ninhydrin treatment of this amino sugar gave a pentose that corresponded to arabinose.

In analogous studies, 8.2 μmol (82%) of UDP-GalNAc and 3.8 μmol (38%) of UDP-glucose were formed from 10 μmol of either GalNAc-1-P or glucose-1-P, and UTP. The characterization of these products was also based on the products produced by phosphodiesterase, mild acid hydrolysis and other treatments.

The products of pyrophosphorolysis, i.e., UTP and HexNAc-1-P, were also identified in the following way: UTP was identified by its mobility on TLC plates as described above, as well as by its UV spectrum and its utilization by diphosphonucleotide kinase. The GlcNAc-1-P and GalNAc-1-P were identified by their susceptibility to alkaline phosphatase and the formation of the appropriate N-acetylhexosamine following this treatment.

No UDP-GlcNAc(GalNAc)-4-epimerase activity could be detected in the purified enzyme preparation. Thus, no GalNAc (or UDP-GalNAc) was detected when UTP and GlcNAc-1-P were incubated with purified enzyme, even though UDP-GlcNAc was rapidly produced and readily detected.

EXAMPLE 18

Photoaffinity Labeling Of The Pyrophosphorylase

Figure 5:
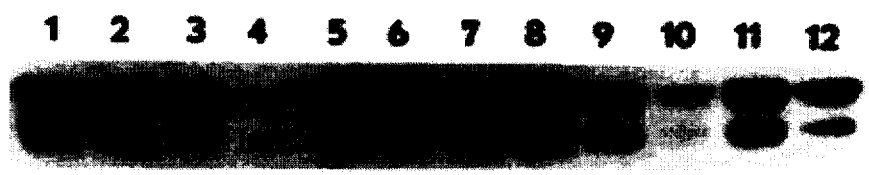
FIG. 5 shows a photoaffinity labeling of purified UDP-GlcNAc pyrophosphorylase with azido-[$^{125}$I]-alkylamine-salicylate-UDP-GlcNAc. Enzyme was incubated with radioactive probe in the presence or absence of various inhibitors, and some of the incubations were exposed to UV light to activate the probe. Each incubation was treated with trichloroacetic acid to precipitate the protein, and the pellet was resuspended in SDS and subjected to SDS-PAGE. Radioactive proteins were detected by exposure to film. Lanes were as follows: 1: no protection; 2: +0.01 mM unlabeled UDP-GlcNAc; lane 3: 0.1 mM UDP-GlcNAc; lane 4: 1 mM UDP-GlcNAc; lane 5: 0.1 mM UDP-GalNAc; lane 6: +1.0 mM 0.1 mM UDP-GalNAc; lane 7: +0.1 mM UDP-Glucose; lane 8: +1.0 mM UDP-Glucose; lane 9: +0.1 mM UTP; lane 10: +1.0 mM UTP; lane 11: +1.0 mM UDP-Gal; lane 12: +1.0 mM UDP-GlcCOOH.

One important use of the purified enzyme of the present invention is for the preparation of azido-UDP[$^{32}$P]-GlcNAc or UDP[32P]-GalNAc. However in order to prepare this analog, it is necessary to have a source of azido-UTP[γ-$^{32}$P]. To prepare this analog, a partially-purified thymidine kinase is needed to react with azido-uridine and ATP[γ$^{32}$P]. An azido and radioactive analog of UDP-GlcNAc was synthesized by attaching a salicylic acid to the uridine through an allylamine to make 5-azido-salicylic-[$^{125}$I]-allylamine-UDP-GlcNAc (ASA-UDP-GlcNAc). This probe proved to be a useful label for UDP-GlcNAc-recognizing enzymes as shown in FIG. 5. In this case, the purified UDP-GlcNAc pyrophosphorylase was incubated for a short time with this probe, exposed to UV light, and the reaction mixture was treated with trichloroacetic acid to precipitate the protein. In each case, the precipitate was isolated by centrifugation, suspended in SDS and subjected to SDS-PAGE.

As shown in lane 1 of FIG. 5, both the 64 kDa and the 55 kDa subunits of the enzyme became labeled with the probe, indicating that both recognized the UDP-GlcNAc product (or substrate). As seen in lanes 2, 3, 4, increasing amounts of unlabeled UDP-GlcNAc (from 0.01 mM to 1 mM), effectively inhibited the labeling of both subunits to about the same extent. This labeling of both subunits was also blocked, although not nearly as effectively, by unlabeled UDP-GalNAc as shown in lanes 5, 6, 7. UDP-glucose also inhibited the labeling but was considerably less effective than either UDP-GlcNAc or UDP-GalNAc. A variety of other nucleoside diphosphate sugars were also examined to determine the specificity of labeling, including UDP-galactose, UDP-xylose, UDP-glucuronic acid and GDP-mannose. None of these sugar nucleotides showed any inhibition of the labeling by 5-azido-ASA-UDP-GlcNAc, even at 1 mM concentrations. In addition, very little inhibition of labeling was seen in the presence of ATP, GTP, GDP, UTP and UDP, although a small effect was seen with UMP. Thus, this photoaffinity label is a useful probe for at least some of the UDP-GlcNAc utilizing or recognizing enzymes.

EXAMPLE 19

Characterization Of The Protein Portion Of The UDP-GlcNAc Pyrophosphorylase

Figure 6:
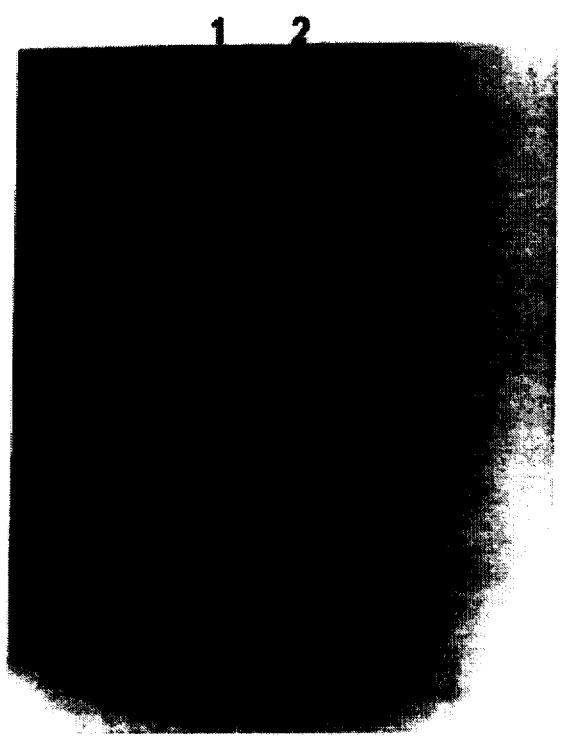
FIG. 6 shows an immunoblotting of UDP-GlcNAc pyrophosphorylase subunits with polyclonal antibody against the native enzyme. Purified enzyme was subjected to SDS-PAGE and stained with Coomassie Blue as seen in lane 1, or exposed to polyclonal antibodies followed by $^{125}$I-anti-rabbit IgG. Lane 2 was exposed to film to detect labeled antibodies.

Polyclonal antibodies against the native enzyme were used in Western blots to detect the enzyme subunits as shown in FIG. 6. As seen in lane 1, two protein bands were detected by Coomassie blue staining which had molecular weights of about 64 and 55 kDa. Lane 2 shows that antibody prepared against the native enzyme reacted with these two bands, and no other protein bands were detected in this preparation. Antibodies against the native enzyme were also effective in removing the enzyme activity from solution when the enzyme preparation was first incubated with antibody followed by a mixture of protein A-Sepharose and protein G-Sepharose.

The two subunits of the pyrophosphorylase were separated on SDS gels and each band was rerun on another gel to be certain that it was homogeneous. The peptides were then transferred to immobilon membranes and subjected to amino acid sequencing on the Applied Biosystems sequencing apparatus.

EXAMPLE 20

UDP-GlcNAc pyrophosphorylase is an important enzyme in eucaryotic cells because it is responsible for the formation of UDP-GlcNAc which is an essential precursor for the GlcNAc residues in N-linked oligosaccharides, proteoglycans, glycolipids, mucins, O-linked oligosaccharides and O-linked GlcNAc. In addition, it is an essential component of the cell walls of yeast and fungi, and is also a key component (or precursor) of the peptidoglycan of many procaryotic cells. In spite of the great diversity of this sugar, there have been only sparse reports on the purification of this key enzyme and none of these purifications have resulted in homogeneous enzyme.

The present invention demonstrated a single band on native gels and this preparation gave rise to 2 protein bands on SDS-PAGE. Since the apparent molecular weight of the native enzyme was about 125 kDa based on gel filtration, and the two subunits appear to have molecular weights of 64 and 55 kDa on SDS gels, the enzyme is most likely a heterodimer. Both of these subunits apparently interact with and recognize UDP-GlcNAc since they both become labeled with the azido-[$^{125}$I]-salicyclic acid-allylamine-UDP-GlcNAc, and in both cases the labeling is blocked by the addition of unlabeled UDP-GlcNAc. Based on these studies, this enzyme is useful for the preparation of a UDP-GlcNAc photoaffinity probe as a tool to identify and purify GlcNAc transferases involved in the formation of various complex carbohydrates. Unfortunately, it is not easy to prepare azido-UTP labeled in the α-phosphate. This should be possible using thymidine kinase and azido-uridine in the presence of ATP[y-$^{32}$P] to make azido-UMP[$^{32}$P] and then phosphorylating this monophosphate with other kinases to produce azido-UTP[$^{32}$P]. In the meantime, the synthetic analog, azido-[$^{125}$I]-salicyclic acid-allylamine-UDP-GlcNAc has been made which does label the pyrophosphorylase and some GlcNAc transferases.

Interestingly enough, the UDP-GlcNAc pyrophosphorylase also works quite well with UDP-GalNAc as a substrate. In fact, both the forward reaction (i.e., UTP+HexNAc-1-P→UDP-HexNAc+PPi), or the backward reaction (i.e., UDP-HexNAc+PPi→HexNAc-1-P+UTP) shows a slightly faster reaction rate with GalNAc substrates than with GlcNAc substrates. Whether this enzyme could actually be involved in the formation of UDP-GalNAc is not known, but liver or kidney have a GalNAc kinase that forms GalNAc-1-P. This activity has recently been detected from pig kidney and partially purified and this partially purified enzyme preparation phosphorylates GalNAc to form GalNAc-1-P but not GlcNAc, galactose or glucose.

The current literature indicates that the formation of UDP-GalNAc involves the action of a 4-epimerase on UDP-GlcNAc to produce UDP-GalNAc. In fact, a mutant CHO cell line has been isolated which is missing the UDP-GlcNAc:UDP-GalNAc 4-epimerase, and this cell line cannot produce O-linked oligosaccharides. Thus, in those cells it appears that epimerization of UDP-GlcNAc is necessary for formation of UDP-GalNAc. However, the kidney may have an alternate pathway to reutilize GalNAc by a kinase and a pyrophosphorylase. In any case, the UDP-GlcNAc (GalNAc) pyrophosphorylase can also be used, in one embodiment of the present invention, to make a UDP-GalNAc photoaffinity probe that should be valuable for the identification, quantification and purification of GalNAc transferases.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. The enzyme UDP-N-acetylglucosamine pyrophosphorylase isolated and purified to homogeneity from pig liver, wherein said enzyme has a molecular weight of about 125 kilodaltons when analyzed by sodium dodecyl sulfate polyacrylamide gel electrophoreses, has an optimal pH of from about pH 8.5 to about 8.9, the purified enzyme being stable for at least four months when stored at $-35°$ C. and wherein said enzyme catalyzes the formation of UDP-N-acetylglucosamine.

2. The enzyme of claim 1, wherein said enzyme requires manganese for optimal activity.

3. The enzyme of claim 1, wherein said enzyme also catalyzes the pyrophosphorylsis of UDP-N-acetylgalactosamine and UDP-glucose.

* * * * *